US008697095B1

(12) United States Patent
Medveczky et al.

(10) Patent No.: US 8,697,095 B1
(45) Date of Patent: Apr. 15, 2014

(54) INHIBITION OF REPLICATION OF ONCOGENIC HERPESVIRUSES

(75) Inventors: Maria M. Medveczky, Tampa, FL (US);
Peter G. Medveczky, Tampa, FL (US);
Tracy Sherwood, Riverview, FL (US);
Thomas W. Klein, Tampa, FL (US);
Herman Friedman, Tampa, FL (US)

(73) Assignee: University of South Florida, Tampa, FL (US)

( * ) Notice: Subject to any disclaimer, the term of this patent is extended or adjusted under 35 U.S.C. 154(b) by 1032 days.

(21) Appl. No.: 11/162,582

(22) Filed: Sep. 15, 2005

Related U.S. Application Data

(60) Provisional application No. 60/612,893, filed on Sep. 24, 2004.

(51) Int. Cl.
*A61K 9/00* (2006.01)

(52) U.S. Cl.
USPC ........................................................ 424/400

(58) Field of Classification Search
USPC ........... 514/454, 169; 424/45, 455, 93.2, 454, 424/4, 9.322
See application file for complete search history.

(56) References Cited

U.S. PATENT DOCUMENTS

| | | | | |
|---|---|---|---|---|
| 5,605,928 A | * | 2/1997 | Mechoulam et al. | 514/454 |
| 2002/0136752 A1 | * | 9/2002 | Whittle et al. | 424/435 |

OTHER PUBLICATIONS

Hitti, "Marijuana May Yield Cancer-Fighting Drugs." Cannabis News at http://cannabisnews.com/news/19/thread19489.shtml.*
Mishkin et al., "Delta-9-Tetrahydrocannabinol Decreases Host Resistance to Herpes Simplex Virus Type 2 Vaginal Infection in the B6C3F1 Mouse." Journal of General Virology 1985: 66; 2539-49.*
Crawford, "Biology and disease associations of Epstein-Barr virus." Phil. Trans. R. Soc. Lond. B 2001: 356;461-473.*
Medveczky et al., "Delta-9 tetrahydorcannabinol (THC) inhibits lytic replication of gamma oncogenic herpes in vitro." BioMed Central Medicine 2004:2;34-42.*
Chen et al., "Cannabinoids Protect Cells from Oxidative Cell Death: A Receptor-Independent Mechanism." The Journal of Pharmacoogy and Experimental Therapcutics 2000:293;807-812.*
Roth et al., "Effects of delta-9-tetrahydrocannabinol on human immune function and host defense." Chemistry and Physics of Lipids 2002:121;229-239.*
Blevins et al., "The Effect of delta-9-Tetrahydrocannabinol on Herpes Simplex Virus Replication." J.gen. Virol. 1980:49;427-431.*
Kimura et al., "Clinical and virologic characteristics of chronic active Epstein-Barr virus infection." Blood 2001:98(2);280-286.*
Emanuel et al., "A Human Monoclonal Antibody to Cytomegalovirus (CMV)." The Journal of Immunology 1984:133(4);2202-5.*
Budt, et al., 2010, "Construction of a Lytically Replicating Kaposi's Sarcoma-Associated Herpesvirus", Journal of Virology, vol. 85, No. 19, pp. 10415-10420.

cdc.gov, "Epstein-Barr Virus and Infectious Mononucleosis", http://www.cdc.gov/ncidod/diseases/ebv.htm, Accessed on Feb. 22, 2012.
Goldstein, et al., "Burkitt's Lymphoma and the Role of Epstein-Barr Virus", Oxford Journals, http://tropej.oxfordjournals.org/content/36/3/114.abstract, Accessed on May 23, 2011.
Gradoville, et al., 2000 "Kaposi's Sarcoma-Associated Herpesvirus Open Reading Frame 50/Rta Protein Activates the Entire Viral Lytic Cycle in the HH-B2 Primary Effusion Lymphoma Cell Line", Journal of Virology, vol. 74, No. 13, pp. 6207-6212.
merriam-webster.com, Inhibit—Definition and More from the Free Merriam-Webster Dictionary,: http://www.merriam-webster.com/dictionary/inhibit, Accessed on Feb. 8, 2012.
dictionary.com, Inhibit—Define Inhibit at Dictionary.com,: http://dictionary.reference.com/browse/inhibit, Accessed on Feb. 8, 2012.
Lukac, et al., 1999, "Transcriptional Activation by the Product of Open Reading Frame 50 of Kaposi's Sarcoma-Associated Herpesvirus is Required for Lytic Viral Reactivation in B Cells", Journal of Virology, vol. 73, No. 11, pp. 9348-9361.
Ragoczy, et al., 1998, "The Epstein-Barr Virus Rta Protein Activates Lytic Cycle Genes and Can Disrupt Latency in B Lymphocytes", Journal of Virology, vol. 72, No. 10, pp. 7978-7984.
Ragoczy, et al., 1999, "Role of the Epstein-Barr Virus Rta Protein in Activation of Distinct Classes of Viral Lytic Cycle Genes", Journal of Virology, vol. 73, No. 12, pp. 9858-9866.
Sun, et al., 1998, "A Viral Gene That Activates Lytic Cycle Expression of Kaposi's Sarcoma-Associated Herpesvirus", Proc. Natl. Acad. Sci., USA, 95, pp. 10866-10871.
Klein, T.W.; Cabral, G.A. 2006. Cannabinoid-Induced Immune Suppression and Modulation of Antigen-Presenting Cells. J Neuroimmune Pharmacol. 1:50-64.
Mbvundula, E.C.; Rainsford, K.D.; Bunning, R.A.D. 2004. Cannabinoids in pain and inflammation. Inflammapharmacology. vol. 12, No. 2: 99-114.
Ambinder. 2000. "Gammaherpesviruses and "Hit-and-Run" Oncogenesis." American Journal of Pathology. vol. 156. No. 1. pp. 1-3.
Bellan et al. 2002. "Burkitt's Lymphoma: New Insights into Molecular Pathogenesis." J. Clin. Pathol. vol. 56. pp. 188-193.
Chang et al. 1998. "Role of Rta in the Translation of Bicistronic BZLF1 of Epstein-Barr Virus." Journal of Virology. vol. 72. No. 6. pp. 5128-5136.
Frangou et al. 2005. "Epstein-Barr Virus (EBV) Infection in Epithelial Cells In Vivo: Rare Detection of EBV Replication in Tongue Mucosa but Not in Salivary Glands." The Journal of Infectious Disease. vol. 191. pp. 238-242.
Herrmann et al. 2002. "Epstein-Barr Virus Replication in Tongue Epithelial Cells." Journal of General Virology. vol. 83. pp. 2995-2998.
Mauser et al. 2002. "The Epstein-Barr Virus Immediate-Early Protein BZLF1 Regulates p53 Function Through Multiple Mechanisms." Journal of Virology. vol. 76. No. 24. pp. 12503-12512.
Sun et al. 1999. "Kinetics of Kaposi's Sarcoma-Associated Herpesvirus Gene Expression." Journal of Virology. vol. 73. No. 3. pp. 2232-2242.

(Continued)

*Primary Examiner* — Brian Gulledge
*Assistant Examiner* — Celeste A Roney
(74) *Attorney, Agent, or Firm* — Michele L. Lawson; Robert Varkonyi; Smith & Hopen, P.A.

(57) ABSTRACT

A method of treating gamma oncogenic herpesviruses, in vivo, through use of Delta-9 Tetrahydrocannabinol (THC). THC inhibits KSHV and EBV reactivation as well as inhibiting lytic replication of MHV 68 and HVS in vitro. Specifically, THC inhibits immediate early gene ORF 50 promoter activity.

9 Claims, 3 Drawing Sheets

(56) References Cited

OTHER PUBLICATIONS

Walling et al. 2001. "Persistent Productive Epstein-Barr Virus Replication in Normal Epithelial Cells In Vivo." The Journal of Infectious Diseases. vol. 184. pp. 1499-1507.

Bellan et al. 2005. "Immunoglobulin Gene Analysis Reveals 2 Distinct Cells of Origin for EBV-Positive and EBV-Negative Burkitt Lymphomas." Blood. vol. 106. No. 3. pp. 1031-1036.

Brady et al. 2008. "Epstein-Barr Virus and Burkitt Lymphoma." Postgrad. Med. J. vol. 84. pp. 372-377.

Damania et al. 2000. "Signaling Activities of Gammaherpesvirus Membrane Proteins." Journal of Virology. vol. 74. No. 4. pp. 1593-1601.

Gradoville et al. 2000. "Kaposi's Sarcoma-Associated Herpesvirus Open Reading Frame 50/Rta Protein Activates the Entire Viral Lytic Cycle in the HH-B2 Primary Effusion Lymphoma Cell Line." Journal of Virology. vol. 74. No. 13. pp. 6207-6212.

Martinez-Guzman et al. 2003. "Transcription Program of Murine Gammaherpesvirus 68." Journal of Virology. vol. 77. No. 19. pp. 10488-10503.

Shlapatska et al. 2004. "Signal Transduction Pathways in Burkitt's Lymphoma Cell Lines BL41 and DG75 with Different Sensitivity to Doxorubicine." Exp. Oncol. vol. 26. No. 3. pp. 210-216.

Teva. 2005. "Vincasar Injection Material Safety Data Sheet." Teva Parenteral Medicines. www.newsicor.com.

Medveczky et al.; Delta-9 tetrahydrocannabinol (THC) inhibits lytic replication of gamma oncogenic herpesviruses in vitro; Sep. 15, 2004; BMC Medicine.

* cited by examiner

| Treatment of NIH 3T3 cells | MHV 68 ORF 50 promoter (firefly luciferase) | CMV renilla luciferase |
|---|---|---|
| DMSO | 100% +/- 14% | 100% +/- 11% |
| 5 µg/ml THC | 13.5% +/- 1.5% | 65.8% +/- 9% |

| Treatment of BCBL-1 cells | KSHV ORF 50 (firefly luciferase) | CMV renilla luciferase |
|---|---|---|
| DMSO | 100% +/- 14% | 100% +/- 3% |
| 5 µg/ml THC | 28% +/- 13% | 128% +/- 3% |

FIGURE 4

| Inhibitor compound | KSHV IC$_{50}$ (μM) | Cellular IC$_{50}$ (μM) | Selectivity index (viral versus cellular IC$_{50}$) |
|---|---|---|---|
| Acyclovir | 75 [ref. 32] | Not done | |
| Ganciclovir | 5.1 [ref. 32] | Not done | |
| Foscarnet | 97 [ref. 32] | Not done | |
| Cidofovir | 0.05 [ref. 32] | Not done | |
| THC | 3.3 (this work) | 33 (this work) | 10 (this work) |
| | MHV 68 IC$_{50}$ (μM) | | |
| Acyclovir | 6 [ref. 34]<br>100 [ref. 33] | 182 [ref. 34] | 30 [ref. 34] |
| Ganciclovir | 28 [ref. 34] | 108 [ref. 34] | 3.7 [ref. 34] |
| Foscarnet | 120 [ref. 34] | 1413 [ref. 34] | 11 [ref. 34] |
| Cidofovir | 0.08 [ref. 34] | 78 [ref. 34] | 10,000 [ref. 34] |
| THC | 1.9 (this work) | 99 (this work) | 52 (this work) |

INHIBITION OF REPLICATION OF ONCOGENIC HERPESVIRUSES

CROSS REFERENCE TO RELATED APPLICATIONS

This application claims priority to U.S. Provisional Patent Application 60/612,893, entitled "Delta-9 Tetrahydrocannabinol (THC) Inhibits Lytic Replication of Gamma Oncogenic Herpesviruses In Vitro," filed Sep. 24, 2004, the text of which is incorporated herein by reference.

BACKGROUND OF THE INVENTION

The Kaposi's Sarcoma-Associated Herpesvirus (KSHV/HHV-8) is the likely cause of Kaposi's sarcoma in AIDS patients, aging individuals and organ transplant patients. KSHV is also implicated in AIDS-associated primary effusion lymphoma (PEL) and a subset of cases of the lymphoproliferative disorder multicentric Castleman's disease. Epstein-Barr virus (EBV) belongs to the same group of herpesviruses and is also involved in human malignancies such as Burkitt's lymphoma, Hodgkin's disease, nasopharingeal carcinoma, and AIDS-associated lymphoma. Related viruses such as herpesvirus saimiri (HVS) of monkeys and the murine gamma herpesvirus 68 (MHV-68) have been developed as animal models. The DNA genomes of these oncogenic viruses persist in nuclei of lymphoid cells in a latent episomal circular form and a few of these cells can produce small amounts of infectious virus in response to extracellular signals, the latent virus can be reactivated leading to production of more infectious virus progeny. This switch from latent to lytic infection is thought to be important in the pathogenesis of herpesviruses and the spread of infection within the organism and among individuals.

Reactivation of latent virus is often initiated by extracellular signals activating through receptors and various transcription factors. Transcription factors activate the promoter of the critical viral gene open reading frame 50 (ORF 50) of KSHV, HVS, MHV 68 or its homologue Rta of EBV. The ORF 50 protein is also a transcription factor and further boosts production of its own mRNA. An important function of ORF 50/Rta is to activate early lytic genes involved in DNA synthesis. After synthesis of early proteins, the process culminates with expression of late genes leading to production of virion components, virus assembly, release of progeny virus and cell death.

SUMMARY OF INVENTION

The present invention provides a method of modulating replication of oncogenic herpesviruses in a patient comprising the step of administering a therapeutically effective amount of Tetrahydrocannabinol (THC) to the patient. In a specific embodiment, the oncogenic herpesvirus is a gamma oncogenic herpesvirus (subfamily Gammaherpesvirinae). The method has specific utility in modulating the replication of Epstein Barr virus (EBV) and Kaposi's sarcoma herpesvirus (KSHV/HHV-8). Additionally, a cell permable analog of Tetrahydrocannabinol which does not induce the psychoactive effects of THC can be utilized. The method of claim 1 wherein the oncogenic herpesvirus is a gamma oncogenic herpesvirus.

The present invention also provides a method of modulating the ORF 50 promoter of a herpesvirus comprising the step of administering to a cell infected with said herpesvirus a therapeutically effective amount of Tetrahydrocannabinol (THC), or a cell permeable analog thereof. As with a previous embodiment the oncogenic herpesvirus is a gamma oncogenic herpesvirus selected from the group consisting of Epstein Barr virus (EBV) and Kaposi's sarcoma herpesvirus (KSHV/HHV-8). Administration of THC can occur in vivo.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Pharmaceutical Compositions

The compounds of the present invention (referred to herein as "active compounds") can be incorporated into pharmaceutical compositions suitable for administration. Such compositions typically comprise Δ-9 Tetrahydrocannabinol (THC), or a cell permeable analog thereof, and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral, inhalation, transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Pharmacogenomics

Agents, or modulators which have a stimulatory or inhibitory effect on the immediate early ORF 50 gene promoter activity as identified by a screening assay can be administered to individuals to treat (prophylactically or therapeutically) disorders (e.g., drug-resistance) associated with aberrant immediate early ORF 50 gene promoter. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of the immediate early ORF 50 gene promoter, expression of a target gene nucleic acid, or mutation content of the immediate early ORF 50 gene promoter in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) Clin. Chem. 43(2): 254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms.

Thus, the activity of THC, expression of the immediate early ORF 50 gene promoter, or mutation content of a target gene in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with an immediate early ORF 50 gene promoter modulator.

TERMS

As used herein "Δ-9 Tetrahydrocannabinol," and "THC,", refer to the major psychoactive cannabinoid compound of marijuana. THC has been shown to modulate and primarily suppress immune responses against various pathogens. THC binds to and activates either one of the two cannabinoid receptors (CB1 and CB2) located on the surface of both brain and lymphoid cells. CB1 and CB2 belong to the family of G protein-coupled receptors characterized by seven trans-membrane loops interacting with the ligand on the outer surface of the cell. The receptors also contain an intracellular signaling domain. Several endogenous natural ligands of the CB receptor family termed endo-cannabinoids have been described. One example is anandamide, a lipid eicosanoid compound generated by the arachidonic acid pathway. The CB receptors are conserved through various vertebrate species including mammals and even fish. They have been shown in various tissues to modulate signaling and gene activation in response to short-lived endocannabinoid ligands or THC. However, THC has also been proposed to influence cellular function by other mechanisms due to its hydrophobic nature and likely association with lipid structures such as cell membranes. This membrane-mediated effect is clearly less specific as all types of cells may be subject to it.

As used herein an "analog" of THC refers to a compound which retains chemical structures of THC necessary for functional activity of THC yet which also contains certain chemical structures which differ from THC. An example of an analogue of a naturally-occurring peptide is a peptide which includes one or more non-naturally-occurring amino acids. In a preferred embodiment, the analog of THC possesses the therapeutically effective characteristics of THC described herein while lacking its psycho-active effects.

As used herein, "a clinical response" is the response to treatment with the active compounds of the present invention. Criteria for determining a response to therapy are widely accepted and enable comparisons of the efficacy alternative treatments (see Slapak and Kufe, Principles of Cancer Therapy, in Harrisons's Principles of Internal Medicine, 13$^{th}$ edition, eds. Isselbacher et al., McGraw-Hill, Inc. 1994).

The term "modulating" as used herein means changing, adjusting, or varying a property of a tissue, cell, or molecule. For example, modulation may cause an increase or a decrease in cellular activity, growth, inhibited DNA synthesis, apoptosis or any other biological, functional or immunological properties associated with THC.

A "therapeutically effective amount" of the active compounds containing THC is that amount necessary to provide a clinical response in vivo. The amount of the active compounds containing THC must be effective to achieve a response, including but not limited to inhibition or total prevention of lytic replication, or improvement or elimination of symptoms associated with a herpesvirus infection or other indicators as are selected as appropriate measures by those skilled in the art.

Tissue Culture Cell Lines, Virus, and THC

The following components were used in the development of the current invention: (1) KSHV positive primary effusion lymphoma cell line (BCBL-1 and BC-3); (2) EBV positive P3HR1; (3) MHV 68; (4) NIH3T12 cells; (5) HVS strain 484; (6) and Owl monkey kidney (OMK) cells. THC was obtained from the National Institute on Drug Abuse, NIH (Bethesda, Md., USA). Three independent batches of synthetic THC were tested that gave very similar results. The purity of these THC preparations exceeded 99%.

Antiviral Assay Based on the Gardeila Gel Method

Cell suspensions were loaded in wells of a vertical agarose gel. The cell layer was then overlaid with a lysis solution containing SDS and pronase resulting in gentle cell lysis and liberation of cellular and viral DNA. The gel was subjected to electrophoresis. Latent episomal DNA migrates much more slowly in these gels than linear replicating DNA. After electrophoresis, southern blotting was performed; DNA was transferred to nitrocellulose followed by hybridization with radiolabeled cloned viral DNA. Radioactive images were analyzed and quantitated by a phospho-imager. The antiviral effect (IC5O) was quantitated by comparing the values obtained from the episomal bands with those from linear bands.

Virus Yield Reduction and Cytotoxicity Assays

NIH3T12 cells were infected with MHV 68, OMK cells with HVS, and both cell types with HSV-1 at a multiplicity of infection of 2 in the presence or absence of various concentrations of THC dissolved in DMSO. Control cultures were treated with DM50. IC50 was determined by measuring virus titers in THC treated and control samples after one cycle of freeze-thawing of the cultures. Additional controls were uninfected cells grown in the presence of THC or DMSO. THC or DMSO were present throughout the experiment.

Dual Luciferase Promoter Assays

A DNA fragment corresponding to the promoter region upstream of the mapped mRNAs was cloned into the basic firefly luciferase vector (Promega, Inc, Madison Wis.) to evaluate the effect of THC on the KSHV ORF 50 promoter. To assay the effect of THC on the MHV 68 ORF 50 gene, a DNA fragment containing the 0.4 kb full length ORF 50 promoter (nucleotides 66242-66652) cloned upstream of the firefly luciferase was utilized. About 5 μg KSHV ORF 50 firefly plasmid DNA was transfected into BCBL-1 cells. About 5 μg MHV 68 ORF 50 firefly plasmid DNA was transfected Into NIH312 cells. Control *renilla luciferase* expression vector (under the control of the CMV immediate early promoter) was included and co-transfected along with the ORF 50 reporter constructs. Cells were incubated for 48 hours with either 5 μg/ml THC solution or an equal amount of DMSO. Luciferase activities were determined using a dual luminometer.

THC Inhibits KSHV and EBV DNA Replication

To evaluate the effect of THC on KSHV replication, the inventors selected BCBL-1 and BC-3 lymphoblastoid cells because these cultures spontaneously produce small amounts of virus, and used a previously published antiviral drug testing protocol to determine whether THC induces or inhibits virus replication (see Medveczky et al., In vitro antiviral drug sensitivity of the Kaposi's Sarcoma-Associated Herpesvirus; *Aids* 1997, 11:1327-1332). Dead cells from BCBL-1 or BC-3 lymphoblastoid cell cultures were removed by Ficoll gradients. Cells were cultured In RPMI 1640 growth medium containing 10% serum for 3 days in the presence or absence of various concentrations of THC (dissolved in DMSO). Control cells were cultured in the presence of 0.1% DMSO (this concentration of DMSO was also used in THC treated cultures). Cells were suspended and loaded in wells of a vertical agarose gel, then overlaid with a lysis buffer to remove proteins from DNA. After lysis, slowly migrating episomal DNA representing the resident latent viral genome, and fast migrating linear DNA representing lytic virus replication, were separated by electrophoresis. After electrophoresis, viral DNA was visualized by Southern blotting. Control DMSO-treated BCBL-1 cells spontaneously produce a small amount of linear DNA, indicating lytic replication/reactivation in a subpopulation of the cells. Various concentrations of THC showed concentration-dependent inhibition of linear but not episomal KSHV DNA. These data were reproducible and similar observations were made in five independent experiments. Based on these experiments the inventors calculated the 50% inhibitory concentration (IC50) of THC at 1 μm/ml or about 3.3 μM.

To evaluate whether another KSHV strain is also susceptible to THC, the BC-3 cell line was also tested. In these cells, THC had a similar inhibitory effect on KSHV reactivation as observed with BCBL-1 cells (not shown).

Two experiments analogous to the one described for KSHV were performed with the EBV transformed B cell line P3HR1. P3HR1 cell cultures were grown in the presence of the phorbol ester TPA, because EBV did not reactivate spontaneously and TPA was essential to induce lytic EBV replication. The cultures were also supplemented with either various concentrations of THC dissolved in DMSO or with equivalent volumes of DMSO. In a representative experiment, an autoradiogram indicated that THC inhibited EBV linear DNA synthesis. Based on quantitative analysis of the radioactive bands and extrapolation of data, the 50% inhibitory concentration (IC50) for THC was estimated at around 0.9 μg/ml or about 3.1 μM.

THC Inhibits MHV 68 and HVS Lytic Replication in Monolayer Cells

The inventors examined the effects of THC on the replication of MHV68 and HVS, two rhadinoviruses related to KSHV and to lesser extent to EBV. These viruses can infect monolayer cells and are suitable for testing the effects of compounds on lytic virus replication by virus yield reduction assays, a more widely used test for evaluating antiviral drugs. NIH3T12 cells were infected with MHV68 at a multiplicity of infection of 2 in the presence or absence of various concentrations of THC dissolved in DMSO. Control cultures were treated with DMSO, THC or DMSO was present throughout the experiment. Cell cultures were incubated for 48 hours. A typical full cytopathic effect of MHV 68 was observed in the control infected cell culture treated with DMSO; most adherent cells become detached from the plate, and remaining loosely adhered cells were round and denser than uninfected controls. However, when infected cells were cultured in the presence of 1.25 μg/ml or higher concentrations of THC, they remained indistinguishable from uninfected control cells and remained adhered to the plate. The effect of 0.6 μg/ml of THC was intermediate between uninfected cells and the full cytopathic effect. These results indicated a protective effect of THC against destruction of host cells by the virus and suggested that THC may inhibit MHV 68 replication. Similar results were obtained with HVS In owl monkey kidney cells (not shown).

Figure 1:
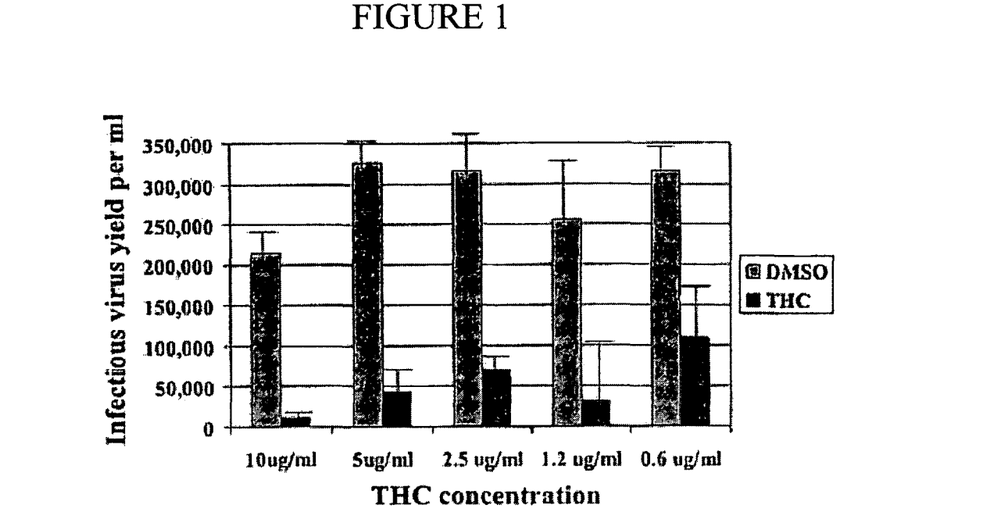
FIG. 1 is a graph showing that THC inhibits MHV 68 virus yield in NIH3T12 cells. NIH3T12 monolayer cultures propagated in 24-well plates were infected and cultured in the presence of various concentrations of THC or equivalent DMSO. Forty-eight hours after infection, control cultures showed complete cytopathic effect and destruction of cells. To liberate cell-associated virus, cultures were subjected to a cycle of freeze-thawing; cells were homogenized and virus was titrated by end point dilution in 96-well plates.

To quantitatively determine antiviral effects of THC, yield reduction assays were performed. NIH3T12 cell cultures were infected with MHV 68 and incubated with THC or DMSO dilutions for 48 hours. Cell-associated virus was liberated by freeze-thawing. After low speed centrifugation, virus titer was determined in the culture supernatants. FIG. 1 shows that virus yield (expressed as infectious units of virus per ml) was highly significantly inhibited by THC Inhibition of virus yield was over 300-fold at 10 μg/ml THC. The 50% inhibitory concentration (IC50) was estimated at around 0.6 μg/ml, equivalent to about 1.9 μM. Similar results were obtained from two independent experiments. Similar and reproducible results were obtained with HVS in monkey kidney cells (not shown).

THC is not Cytotoxic to Murine NIH3T12 or Owl Monkey Kidney (OMK) Cells

Because the observed effects might be due to a non-specific toxic effect of THC, the inventors tested whether THC alters cell division or morphology in NIH3T12 and owl monkey kidney (OMK) cells. Monolayers of these cells were prepared at about 25% confluency and cultured for 2 days in the presence of THC concentrations ranging 0.6-10 μg/ml. THC treated cultures were indistinguishable from control cultures, formed confluent monolayers, and showed no altered morphology. Owl monkey kidney (OMK) cells also showed no toxicity in an analogous experiment (not shown).

The effect of higher THC concentrations on cell division was also determined. Exponentially growing BCBL-1 or NIH12 cells were cultured for two days in the presence of various concentrations of THC or DMSO and cell counts were determined. The 50% cell division inhibitory concentration of THC for BCBL-1 cells was around 33 μM. NIH3T12 cells were less sensitive and the 50% inhibitory concentration was around 99 μM (not shown).

THC has No Comparable Effect on HSV-1 Lytic Replication

The inventors next examined whether or not the THC inhibitory effect can be observed against other herpesviruses and tested whether drug treatment suppresses the replication of the alpha herpesvirus, HSV-1. Monolayers of NIH3T12 were prepared, infected with about 100 infectious units of HSV-1, and cultured for 3 days in the presence of THC concentrations ranging 0.6-10 μg/ml. Typical plaques developed in THC treated cultures, indistinguishable from those in control cultures. HSV-1 replication in OMK was also unaffected by THC in an analogous experiment (not shown).

Figure 2:
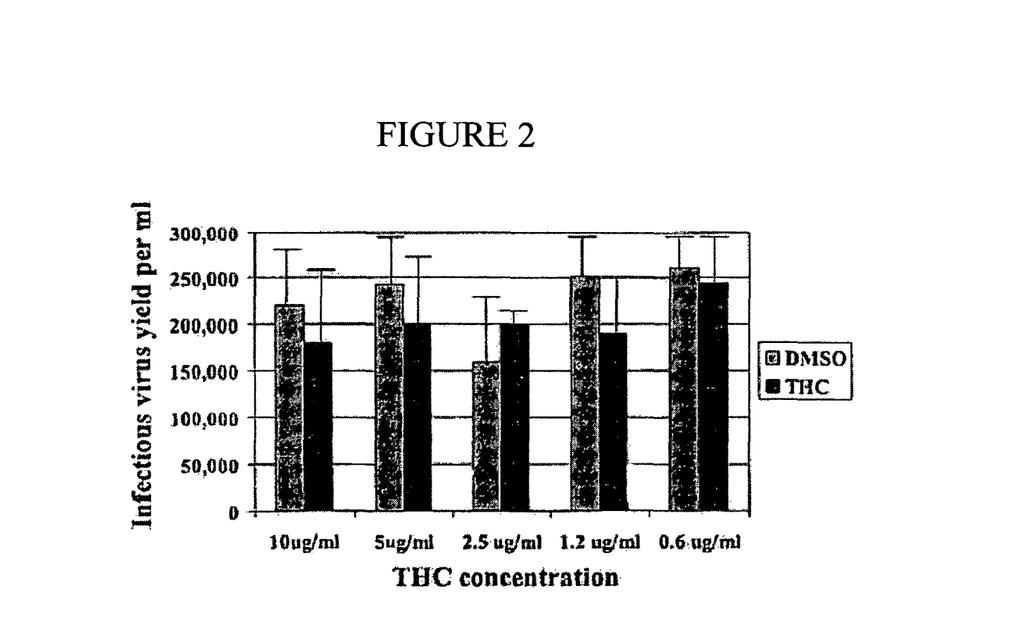
FIG. 2 is a graph showing that THC has no significant effect on virus yield of HSV-1 in NIH3T12 cells. NIH3T12 monolayer cultures propagated in 24-wall plates were infected with HSV-1 at a multiplicity of 2 and cultured in the presence of various concentrations of THC or equivalent DMSO. Twenty-four hours after infection, all cultures showed complete cytopathic effect and destruction of cells. To liberate cell-associated virus, cultures were subjected to a cycle of freeze-thawing; cells were homogenized and virus was titrated.

The inventors also examined the effects of THC on production of HSV-1 virus yield in NIH3T12 cells. Cells were infected with HSV-1 at a multiplicity of infection of 2 in the presence or absence of various concentrations of THC dissolved in DMSO. Control cultures were treated with DMSO. THC or DMSO were present throughout the experiment. Cell cultures were incubated for 24 hours and cell-associated virus was liberated by freeze-thawing. After low speed centrifugation the HSV-1 titer was determined in the culture supernatants. FIG. 2 shows that THC had no significant inhibitory effect on replication of HSV-1 in NIH3T12 cells.

THC Inhibits the ORF 50 Promoter

Figure 3:
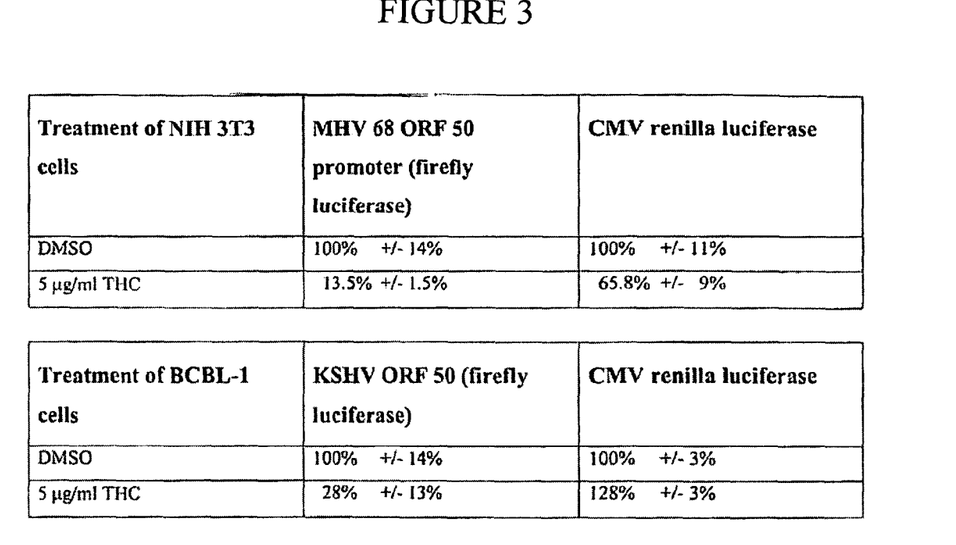
FIG. 3 is a table showing the relative luciferase activity of extracts from control and THC treated cells. NIH 3T3 cells co-transfected with MHV 68 ORF 50 plus CMV control (top rows). BCBL-1 cells were co-transfected with the KSHV ORF 50 plus CMV control (bottom rows). Data represents averages from three independent co-transfection experiments.

To evaluate the effect of THC on the MHV 68 and KSHV ORF 50 promoters, luciferase reporter assays were performed. To assay the effect of THC on the MHV 68 gene, a DNA construct containing the 0.5 kb full length ORF 50 promoter cloned upstream of the firefly luciferase was transfected into NIH3T12 cells. Control *renilla luciferase* expression vector (under the control of the CMV immediate early promoter) was included and co-transfected with the ORF 50 reporter. Cells were incubated for 48 hours with either 5 µg/ml THC or equal amount of DMSO. Luciferase activities were determined using a dual luminometer. The results show (FIG. 3) that 5 µg/ml THC suppressed the ORF 50 promoter about 7.4 fold. In contrast, the control CMV promoter activity was only reduced by 35%. Similar results were obtained with the KSHV ORF 50 promoter construct containing 1 kb of the promoter sequence. In the transfected BCBL-1 cells, 5 µg/ml THC inhibited the ORF 50-driven luciferase activity almost 4-fold. Interestingly, the co-transfected CMV promoter was slightly stimulated by THC in these cells. These results were obtained from three independent transfection experiments for both the MHV 68 and KSHV promoter assays.

Cannabinoid Receptor Antagonists can Reverse the Inhibitory Effect of THC on KSHV Replication.

To investigate whether the observed antiviral effects of THC are mediated through the cannabinoid receptors, two antagonists of THC, SR141716A (which acts on CB1) and SR144528 (which inhibits CB2), were tested in the standard BCBL-1 KSHV reactivation assay. BCBL-1 cells were incubated with or without THC and in the presence of these compounds. The THC Inhibition of KSHV DNA synthesis was not reversed by treatment with a single receptor antagonist (not shown). The antagonists had no effect on spontaneous KSHV reactivation. However, they reversed the inhibition of linear DNA synthesis by 1.25 µg/ml THC.

Figure 4:
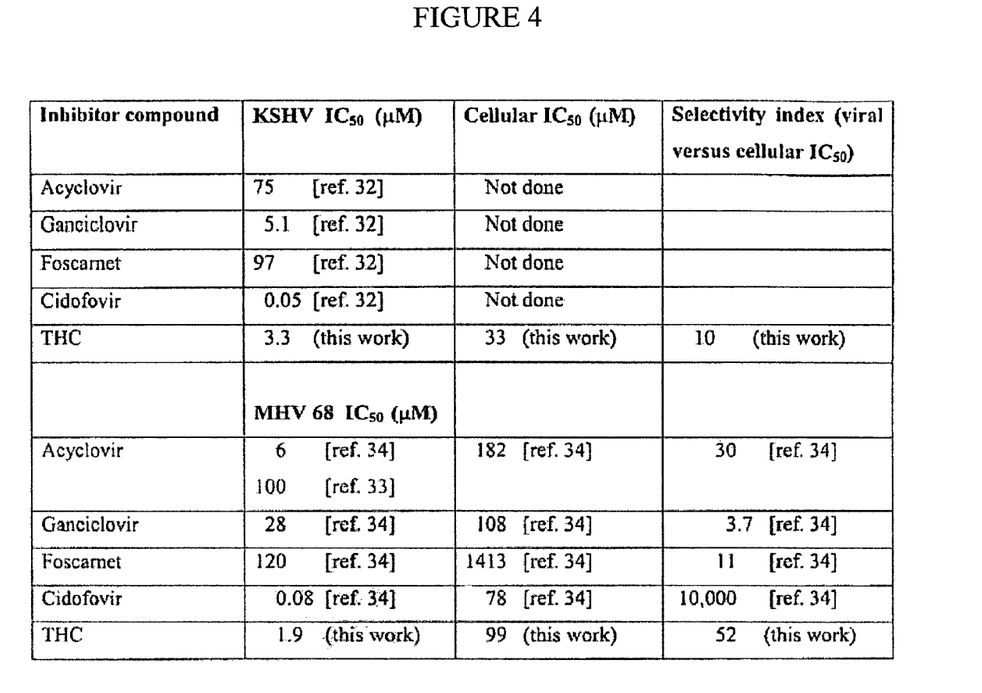
FIG. 4 is a table showing a comparison of 50% antiviral and cell division inhibitory concentrations ($IC_{50}$) and selectivity (virus versus cellular $IC_{50}$) of selected antiviral drugs and THC.

To summarize the antiviral effects of THC and to compare THC with well-characterized antiviral drugs, the inventors compiled data from the literature as well as from their own experimental results. FIG. 4 shows the 50% inhibitory concentrations (IC50) of four known antiviral drugs and of THC. Data on the antiviral effects of acyclovir, PFA and ganciclovir on KSHV were obtained from Gardella gel assays. Usherwood et al also used a Gardella gel-based assay to determine the effect of acyclovir against MHV 68 in transformed B cell line S11. The data regarding the effects of four antiviral drugs against MHV 68 and on cell division are from the work of Neyts and De Clercq using standard lytic virus replication inhibition assays on monolayers. The THC antiviral results are from the data described herein (Gardella gels for KSHV using BCBL-1 cells and NIH12 antiviral assays for MHV 68). These data show that THC is a potent and selective antiviral agent against KSHV comparable with some well-characterized anti-herpesvirus compounds. THC is even more potent and selective against MHV 68 than acyclovir, ganciclovir and foscarnet. Cidofovir appears to be most potent in these in vitro experiments, however, this drug is known to cause serious side effects and is toxic to the kidney in humans.

THC can modulate and inhibit the activation of immune cells, furthermore it can down-regulate the reactivation of viruses residing in lymphocytes, as shown herein. However, the antiviral effect of THC is not cell specific, since MHV 68 and HVS replication was also strongly inhibited by THC in NIH3T12 or owl monkey kidney monolayer cell cultures. This observation shows that THC either directly or indirectly targets a viral gene shared by these herpesviruses.

Data shows that THC may inhibit KSHV replication through the cannabinoid receptors. When BCBL-1 cells were treated with THC the receptor antagonists partially reversed this effect, suggesting a role for the CB receptors expressed by BCBL-1 cells. As discussed, ORF 50/Rta is a critical gene for both reactivation of latent virus and lytic replication in monolayers. Interestingly, ORF 50/Rta activation involves cAMP signaling. In contrast, cannabinoid receptor binding has been shown to down-regulate the level of activated CREB through a decrease in cyclic AMP synthesis. Therefore, one possible explanation is that THC inhibits cAMP signaling, leading to decrease of ORF 50/Rta-mediated transcription and block of virus replication. This antiviral mechanism of THC is supported by the inventors data. Luciferase reporter assays showed that in the presence of THC, initiation of transcription of ORF 50 mRNA in both KSHV and MHV 68 is markedly reduced (4-fold and 0.4-fold, respectively) as compared with the CMV immediate early promoter. These data suggest selective inhibition of the ORF 50 promoter of MHV 68 and KSHV by THC. However, it is also believed that THC also blocks other cellular and viral genes, as this drug has been shown to cause a wide range of changes in lymphocyte gene expression.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of inhibiting lytic replication of oncogenic herpesviruses comprising the step of administering a therapeutically effective amount of Tetrahydrocannabinol to a cell wherein the cell is infected with actively replicating oncogenic herpesvirus;
    wherein the herpesvirus is selected from the group consisting of Epstein Barr virus (EBV) and Kaposi's sarcoma herpesvirus (KSHV/HHV-8).

2. A method of inhibiting the ORF 50 promoter of a herpesvirus comprising the step of administering to a cell infected with an actively replicating herpesvirus a therapeutically effective amount of Tetrahydrocannabinol;
    wherein the herpesvirus is selected from the group consisting of Epstein Barr virus (EBV) and Kaposi's sarcoma herpesvirus (KSHV/HHV-8).

3. The method of claim 2 wherein the therapeutically effective amount of Tetrahydrocannabinol is administered in vivo.

4. A method of inhibiting the ORF 50 promoter of a herpesvirus comprising the step of contacting a cell infected with an actively replicating herpesvirus with a therapeutically effective amount of a cell permeable compound wherein the cell permeable compound is Tetrahydrocannabinol;

wherein the herpesvirus is selected from the group consisting of Epstein Barr virus (EBV) and Kaposi's sarcoma herpesvirus (KSHV/HHV-8);
wherein the therapeutically effective amount of Tetrahydrocannabinol is administered to result in a concentration of between 0.6 µg/ml and 10 µg/ml.

5. The method of claim 4 wherein therapeutically effective amount of the cell permeable compound is administered in vivo.

6. The method of claim 1 wherein the therapeutically effective amount of Tetrahydrocannabinol is administered to result in a concentration of between 0.6 µg/ml and 10 µg/ml.

7. The method of claim 6 wherein the therapeutically effective amount of Tetrahydrocannabinol is administered to result in a concentration of 5 µg/ml.

8. The method of claim 2 wherein the therapeutically effective amount of Tetrahydrocannabinol is administered to result in a concentration of 5 µg/ml.

9. The method of claim 4, wherein the therapeutically effective amount of Tetrahydrocannabinol is administered to result in a concentration of 5 µg/ml.

* * * * *